United States Patent [19]
Christian et al.

[11] Patent Number: 5,433,725
[45] Date of Patent: Jul. 18, 1995

[54] HAND-HELD SURGICAL DEVICE AND TOOLS FOR USE THEREWITH, ASSEMBLY AND METHOD

[75] Inventors: Jeffrey J. Christian, San Jose; Robert D. Berkowitz, Menlo Park; Michael Hogendijk, Sunnyvale; Jeffrey E. Holmes, San Jose, all of Calif.

[73] Assignee: Unisurge, Inc., Cupertino, Calif.

[21] Appl. No.: 806,666

[22] Filed: Dec. 13, 1991

[51] Int. Cl.⁶ .............................................. A61B 17/34
[52] U.S. Cl. .................................. 606/207; 606/174; 128/751; 600/104
[58] Field of Search ........................................ 128/3–6, 128/751–755; 606/174, 205–211, 170, 171, 180, 184, 51, 52; 604/22

[56] References Cited

U.S. PATENT DOCUMENTS

| | | | |
|---|---|---|---|
| 3,989,033 | 11/1976 | Halpern et al. | 606/206 |
| 4,461,305 | 7/1984 | Cibley | 128/751 |
| 4,522,206 | 6/1985 | Whipple et al. | 606/174 |
| 4,674,501 | 6/1987 | Greenberg | 606/174 |
| 4,881,550 | 11/1989 | Kothe | 128/752 |
| 4,994,079 | 2/1991 | Genese et al. | 606/206 |
| 5,286,255 | 2/1994 | Weber | 606/205 |

FOREIGN PATENT DOCUMENTS

| | | |
|---|---|---|
| 23926/88 | 7/1989 | Australia . |
| 73971/91 | 7/1991 | Australia . |
| 27065/92 | 4/1993 | Australia . |

*Primary Examiner*—Stephen C. Pellegrino
*Assistant Examiner*—William Lewis
*Attorney, Agent, or Firm*—Flehr, Hohbach, Test, Albritton & Herbert

[57] ABSTRACT

Hand-held endoscopy assembly for use in performing a medical procedure comprising a hand-held endoscopy device having a bore extending therethrough. A surgical tool is removably mounted in the bore and is retained in a fixed longitudinal position within the device while permitting rotation of the tool in the device. A valve in the bore establishes a substantially fluid-tight seal between the bore and the tool.

14 Claims, 8 Drawing Sheets

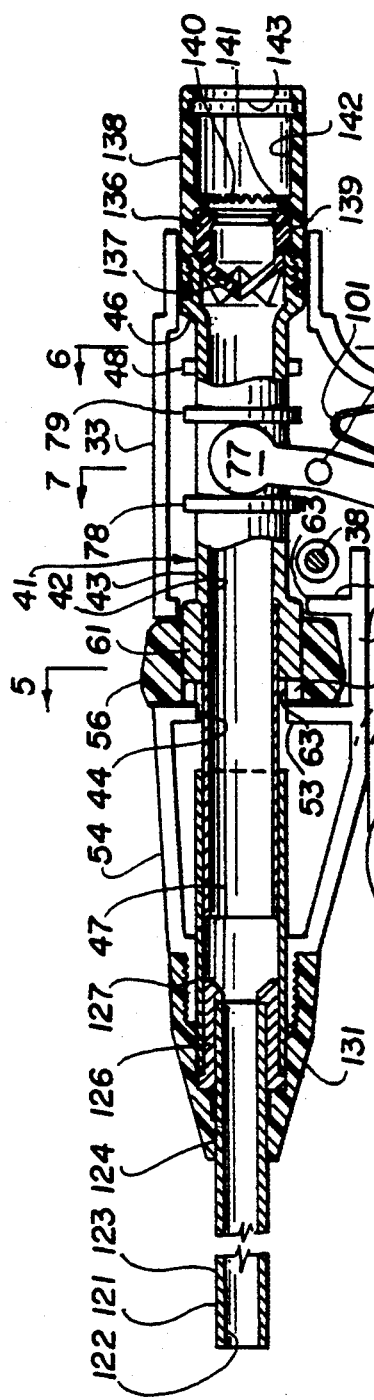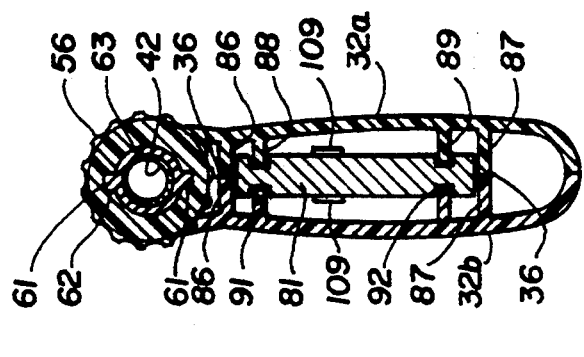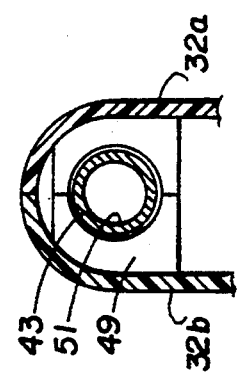
Fig.4
Fig.5
Fig.6

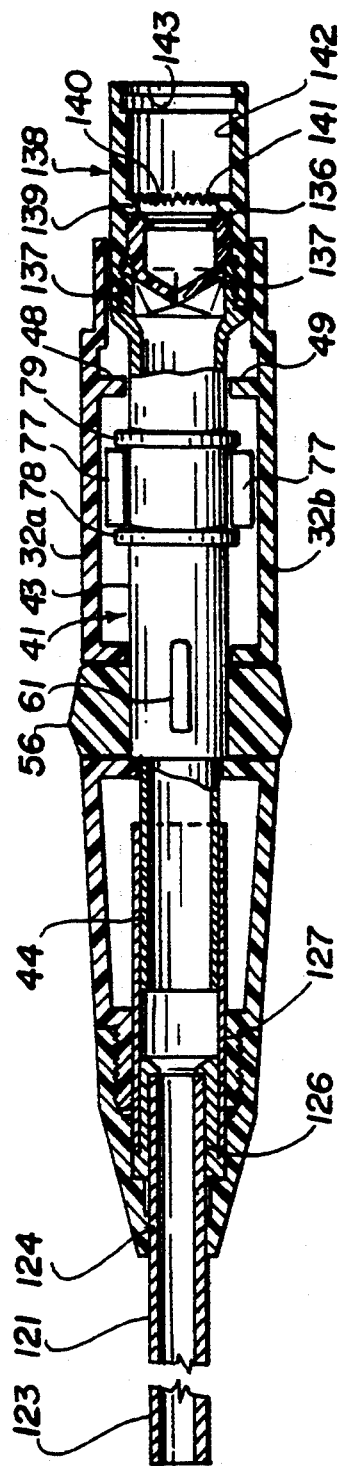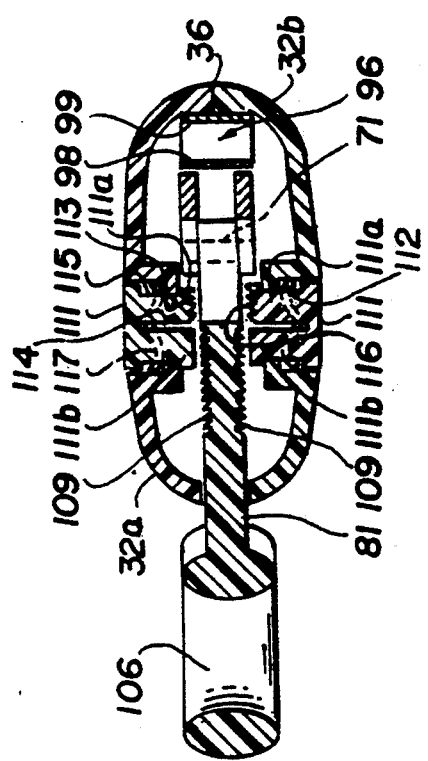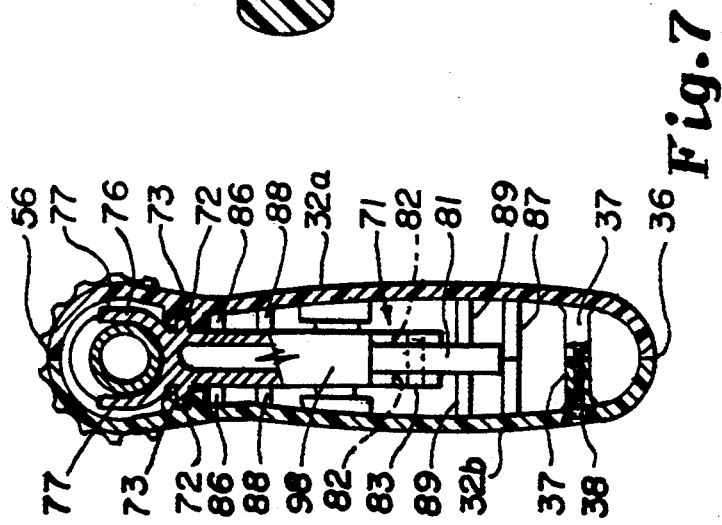

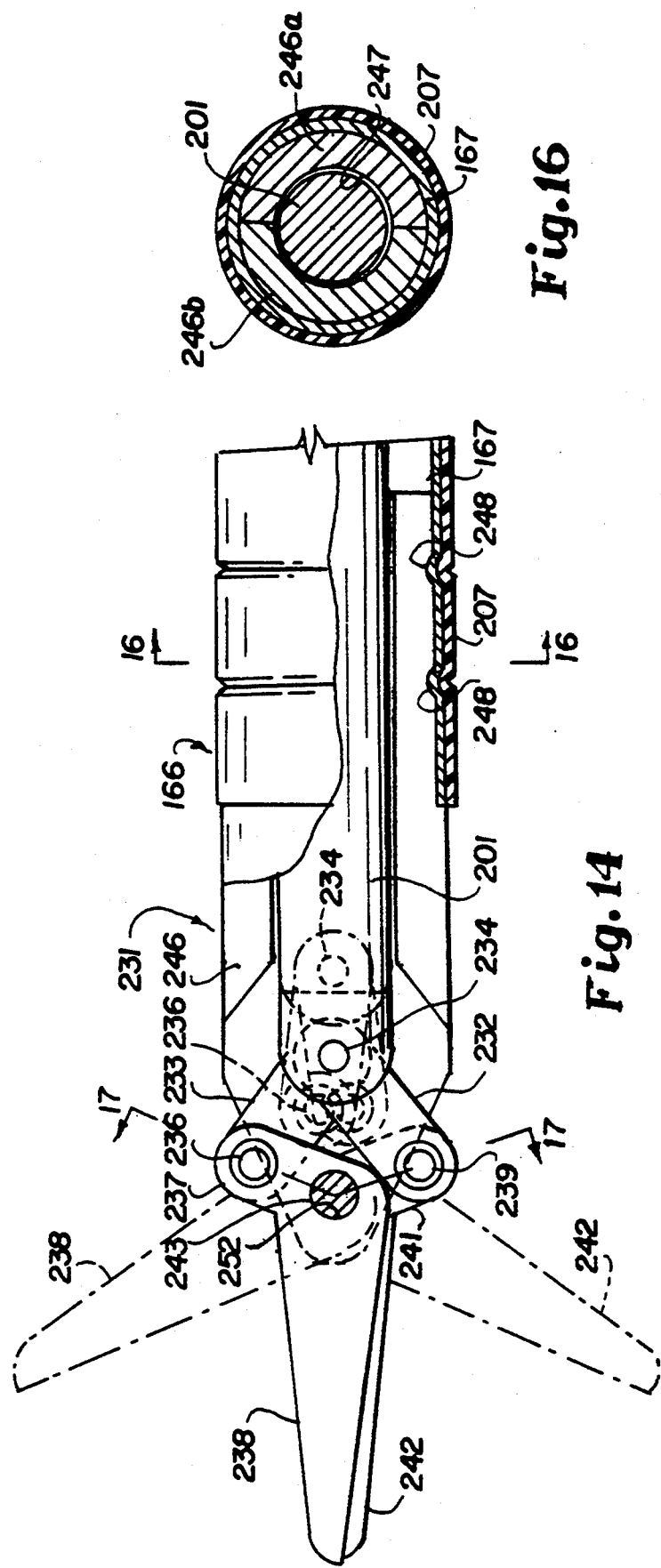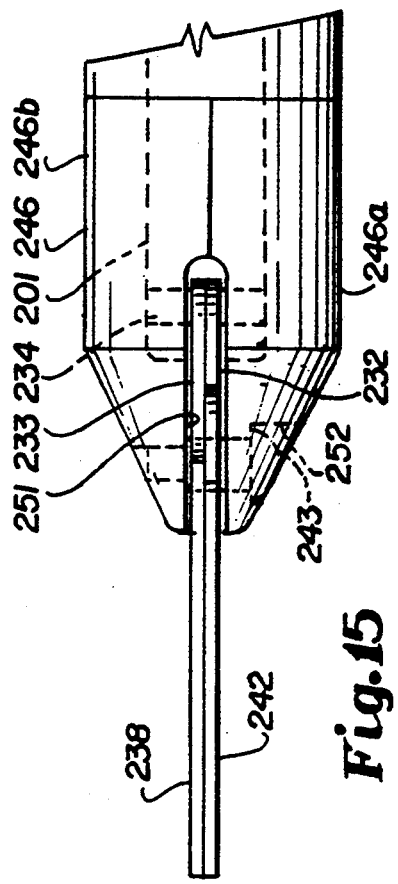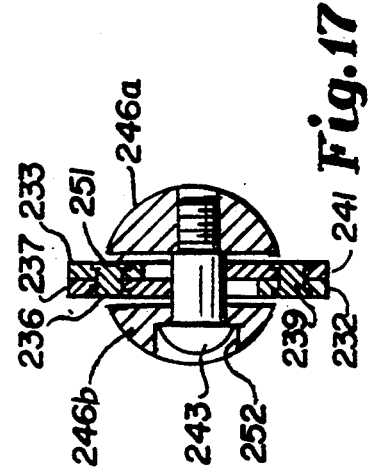

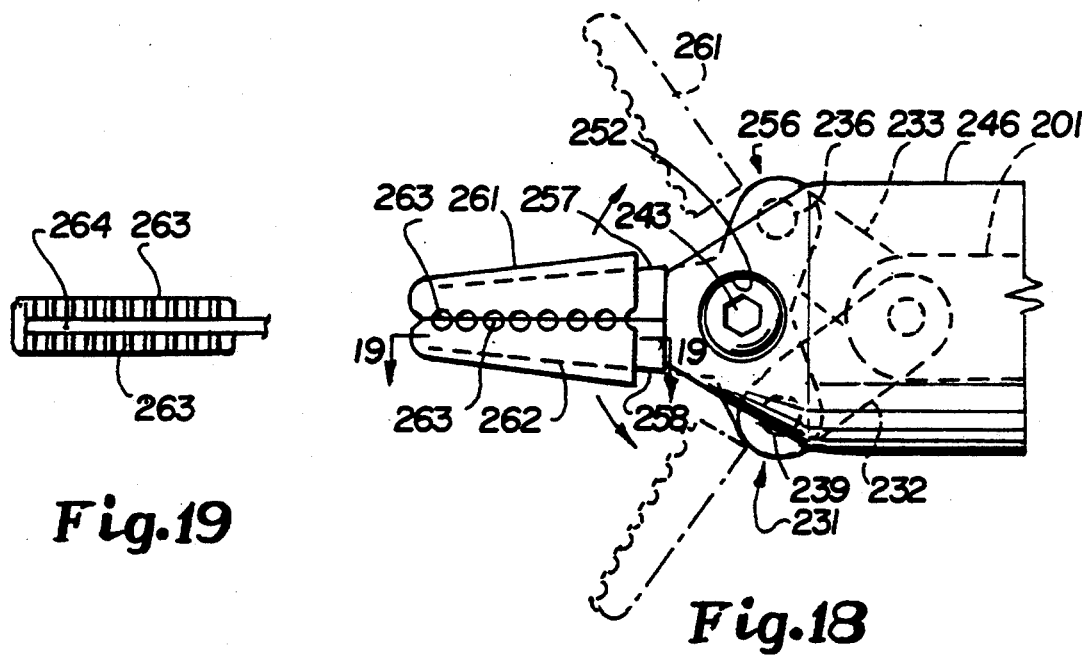
Fig.19
Fig.18
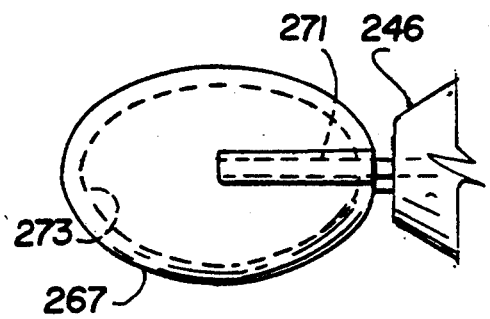
Fig.21
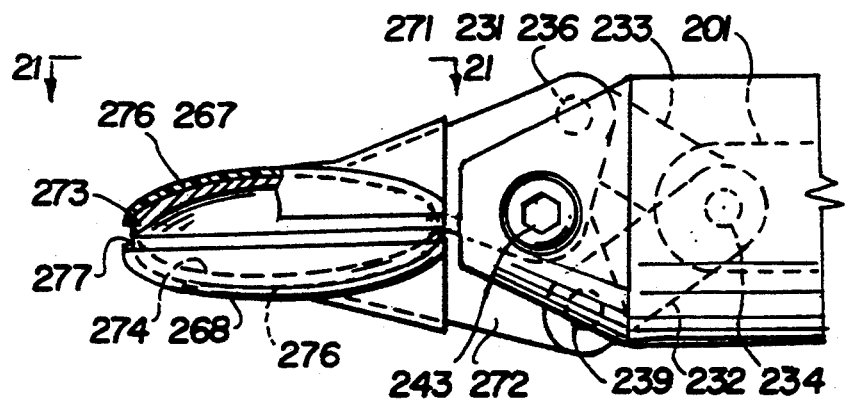
Fig.20

HAND-HELD SURGICAL DEVICE AND TOOLS FOR USE THEREWITH, ASSEMBLY AND METHOD

This invention relates to a hand-held surgical device and tools for use therewith, an assembly and method, and more particularly to such a device, tools, assembly and method for use in performing medical procedures.

Surgical devices for use in endoscopic procedures have heretofore been provided. These typically, however, have been separate individual devices or tools used independently. This is particularly true for tools for use in laparoscopy in which the tools usually have been expensive, fine precision metal tools. There is therefore a need for tools which are much less expensive which can be made disposable if so desired, and which can be utilized in conjunction with a hand-held surgical device.

In general, it is an object of the present invention to provide a hand-held surgical device and tools for use therewith, an assembly and a method for utilizing the same.

Another object of the invention is to provide a device of the above character which is provided with a hollow bore through which the tools can be inserted.

Another object of the invention is to provide a device of the above character in which the device includes a trigger mechanism for causing a linear thrusting motion which is utilized for actuating tools disposed in the bore of the device.

Another object of the invention is to provide a device of the above character in which the bore extends through a slidably mounted sleeve or barrel.

Another object of the invention is to provide a device of the above character in which the sleeve can be rotated.

Another object of the invention is to provide a device of the above character in which the tools can be locked onto the device for actuation of the tools and for rotation of the tool.

Another object of the invention is to provide a device of the above character in which tools can be readily inserted and removed.

Another object of the invention is to provide a device and tools for use therewith of the above character in which substantially fluid-tight seals are created between the tool and the device when a tool is inserted in the device.

Another object of the invention is to provide a device and tools for use therewith of the above character in which spring-loaded members are utilized.

Another object of the invention is to provide a device and tools for use therewith of the above character with which electrocautery operations can be performed.

Another object of the invention is to provide a device and tools for use therewith in which the tools can be made disposable if desired.

Another object of the invention is to provide a device of the above character which can be sterilized.

Additional objects and features of the invention will appear from the following description of the particular embodiment as set forth in detail in conjunction with the accompanying drawings:

FIG. 4 is a cross-sectional view taken along the line 4—4 of FIG. 2.

FIG. 5 is a cross-sectional view taken along the line 5—5 of FIG. 4.

FIG. 6 is a cross-sectional view taken along the line 6—6 of FIG. 4.

FIG. 7 is a cross-sectional view taken along the line 7—7 of FIG. 4.

FIG. 8 is a cross-sectional view taken along the line 8—8 of FIG. 1.

FIG. 9 is a cross-sectional view taken along the line 9—9 of FIG. 1.

FIG. 14 is a partial side elevational view partly in cross-section of the distal extremity of a tool incorporating the present invention.

FIG. 15 is a top plan view of the tool shown in FIG. 14 looking along the line 15—15 of FIG. 14.

FIG. 16 is a cross-sectional view taken along the line 16—16 of FIG. 14.

FIG. 17 is a cross-sectional view taken along the line 17—17 of FIG. 14.

FIG. 18 is a side elevational view of a distal extremity of another tool incorporating the present invention.

FIG. 19 is a view looking along the line 19—19 of FIG. 18.

FIG. 20 is a view of the distal extremity of another tool incorporating the present invention.

FIG. 21 is a top plan view looking along the line 21—21 of FIG. 20.

Figure 1:
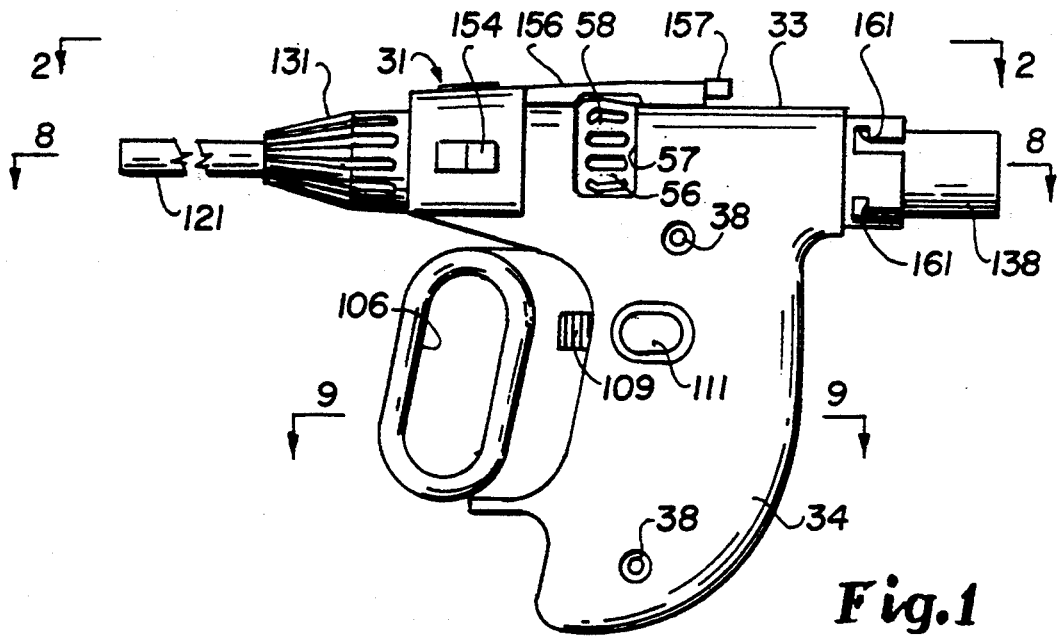
FIG. 1 is a side elevational view of hand-held surgical device incorporating the present invention.
Figure 2:
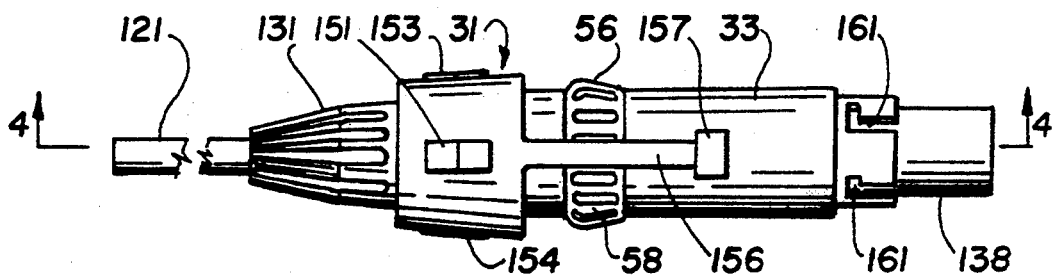
FIG. 2 is a top plan view looking along the line 2—2 of FIG. 1.
Figure 3:
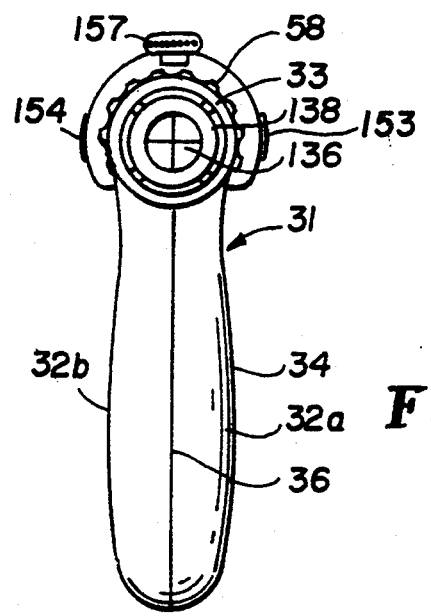
FIG. 3 is a rear elevational view looking along the line 3—3 of FIG. 1.

In general, the hand-held surgical assembly for use in performing a medical procedure is comprised of a hand-held endoscopy device having a bore extending therethrough. It also consists of a tool removably mounted in the bore. Cooperative means is provided for establishing a substantially fluid-tight seal between the bore and the tool. An adapter assembly is mounted on the tool.

More in particular, as shown in the drawings of FIGS. 1-9, the hand-held surgical device 31 consists of a housing 32 which is provided with an upper cylindrical portion 33 and a handle portion 34 in the form of a pistol grip adapted to be grasped and held by a single human hand. The housing 32 is preferably formed of a material which can repeatedly withstand autoclave sterilization, ethylene oxide sterilization or gamma radiation sterilization. One material found to be particularly suitable for this purpose is a plastic identified as Ultem, manufactured by the General Electric Company. Such a material is capable of withstanding high temperatures and is very durable. The housing 32, utilizing such a plastic, is formed in two parts 32a and 32b (see FIG. 3) which are joined together along a parting line 36. A pair of spaced apart bosses 37 (see FIG. 4) are provided on each of the parts 32a and 32b so that the two parts 32a and 32b can be fastened together by suitable means such as screws 38 extending into the bosses and forming the two parts 32a and 32b into a unitary housing 32. An actuator tube assembly 41 is mounted in the upper cylindrical portion 33 for limited axial movement. The actuator tube assembly 41 is provided with a bore 42 which extends therethrough. The actuator tube assembly 41 consists of two tubes 43 and 44 in which tube 43 is formed of a suitable plastic such Ultem, hereinbefore identified, and the tube 44 is formed of a suitable metal such as stainless steel. The metal tube 44 has its proximal extremity fixed within the distal extremity of the plastic tube 43 so that the bore 42 is continuous and has the same diameter extending from the plastic tube 43 into the metal tube 44. The actuator tube assembly 41 is provided with proximal and distal extremities 46 and 47. These proximal and distal extremities 46 and 47 are axially guided within the housing by sidewise extending guide portions 48 and 49 (see FIG. 6) formed integral with the housing parts 32a and 32b having semicircular recesses 51 which are adapted to receive the proximal extremity 46 of the actuator tube assembly 41. Similarly, upper and lower guide portions 53 (see FIG. 4) formed integral with the parts 32a and 32b and having semicircular recesses 54 guide the distal extremity 47 of the actuator tube assembly 41.

Means is provided for rotating the actuator tube assembly 41 about its axis and consists of a thumbwheel or knob 56 (see FIGS. 1 and 4) which encircles the actuator tube assembly 41 and which extends through a slot 57 provided in the housing 32 so that the thumbwheel or knob 56 can be actuated by a finger of the hand while the hand is holding the pistol grip-shaped handle portion 34. The thumbwheel 56 is provided with spaced apart, axially extending raised portions 58 to facilitate frictional engagement by a finger of the wheel or knob 56. Cooperative mating means is provided between the thumbwheel 56 and the plastic tube 43 of the actuator tube assembly 41. The cooperative mating means consists of a pair of diametrically spaced apart axially extending keys 61 which are slidably mounted in the slots 62 extending diametrically outwardly from a bore 63 provided in the thumbwheel 56. The thumbwheel 56 is retained in a fixed longitudinal position with respect to the actuator tube assembly 41 by the guide portions 53 and wall portions 64 formed integral with the housing parts 32a and 32b, and having semicircular recesses 66 (see FIG. 4).

Means is provided for causing reciprocal movement of the actuator tube assembly 41 for a suitable distance, as for example 0.125", and consists of yoke-like lever arm 71 formed of a suitable plastic such as Ultem. The yoke-like member 71 is provided with a pair of pins 72 extending from opposite sides thereof that are pivotally mounted in recesses (see FIG. 7). As can be seen, the pins 72 are provided at the upper extremity of the lever arm formed by the member 71 to provide a substantial mechanical advantage, as for example a 4-to-1 mechanical advantage. The upper extremity of the yoke-like lever arm 71 is provided with a U-shaped or forked portion 76 having generally circular upper extremities 77 (see FIG. 4), which are disposed on opposite sides of the plastic tube 43 between circumferentially extending spaced apart flanges 78 and 79 provided centrally of the plastic tube 43 of the actuator tube assembly 41. As can be seen from FIG. 4, the upper circular extremities 77 fit relatively closely within the flanges 78 and 79. The lower extremity of the yoke-like lever member 71 is pivotally connected to a trigger bar 81 by pin-and-slot connections in which elongate slots 82 are provided on opposite sides of the yoke-like member 71 that receive the opposite extremities of a pin 83 mounted in the trigger bar 81. The trigger bar 81 is mounted within the housing 32 for movement in a direction which is substantially parallel to the axis of the actuator tube assembly 41. The trigger bar 81 travels between upper and lower wall portions 86 and 87 which are formed integral with the housing parts 32a and 32b (see FIG. 5). In addition, the trigger bar 81 is guided by upper and lower guide portions 88 and 89 also formed integral with the housing parts 32a and 32b and which extend inwardly and slidably seat in grooves 91 and 92 provided on opposite sides of the trigger bar 81.

Spring means is provided for yieldably urging the trigger bar 81 to the left as viewed in FIG. 4 and consists of a leaf-spring 96 which has one leaf 97 engaging the interior of the housing 32 and the other end 98 engaging the lower extremity of the yoke-like member 71. The apex 99 of the spring can be secured if desired to the interior of the housing 32 by a screw 101. Means is provided for limiting the travel of the trigger bar 81 to the left in the housing 32 as viewed in FIG. 4, and consists of the yoke-like member 71 which restrains movement of the trigger bar 81 because of the limitations in axial movement of the actuator tube assembly 41 in the upper cylindrical portion 33.

The trigger bar 81 is provided with means whereby it is adapted to be grasped by fingers of the hand holding the handle portion 34. Such means consists of an elongate finger hole 106 which extends in a direction which is generally perpendicular to the axis of movement of the actuator tube assembly 41. It preferably is a size which is adapted to receive at least two fingers of the hand, as for example the two fingers between the index finger and the little finger or the index and middle fingers of the hand.

Means is provided for retaining the trigger bar 81 in a predetermined position against the force of the yieldable means provided by the leaf spring 96 and consists of elongate sawtooth portions 109 which are provided on opposite sides of the trigger bar 81. The portions 109 are adapted to be engaged by plungers 111 seated in a well 112 and extending through a hole 113 provided in the housing 32. Each of the plungers 111 is provided with two portions 111a and 111b with a space 114 therebetween and an annular recess 115 so that the portions 111a and 111b can be pressed together and snapped through the hole 113 and retained therein. The distal extremity of the plunger portion 111a is provided with sawteeth 116 which are adapted to engage the sawteeth of the sawtooth portions 109. A wave washer 117 is provided in each of the wells 112, and is utilized for yieldably returning the finger-operated plunger 111 into an out-of-engagement position. When the plunger 111 is engaged by a finger of the hand, as for example by the thumb on one side or the index finger on another side, the plunger 111 can be pushed inwardly against the force of the wave washers or springs 117 to cause the sawteeth 116 to engage the sawtooth portions 109 to retain the trigger bar 81 in a predetermined position. As soon as the sawtooth are engaged, the frictional engagement is sufficient to prevent the wave washers from returning a plunger 111 to its home position. It is only when the trigger bar 81 is moved that the wave washers 117 will cause the sawteeth 116 to disengage and to permit a plunger 111 to return to its home position.

The surgical device 31 also includes a barrel 121 which is provided with a bore 122 extending axially thereof and through the barrel 121. The barrel 121 can be formed of a suitable material such as stainless steel. The bore 122 can be of a suitable size, as for example 8 mm. However, it should be appreciated that in connection with the present invention different barrels with different size bores can be provided, as for example ranging from 6 to 12 mm bores. The barrel can have a suitable length, as for example 8 to 14 inches. It is provided with a distal extremity 123 and a proximal extremity 124. The proximal extremity 124 is mounted within an adapter 126 of Ultem in the form of a reducer that is mounted in a metal tube 127 of a larger diameter. The diameter of the metal tube 127 is such so that the distal extremity of the metal tube 44 can slidably fit therein to provide a substantially fluid-tight seal between the same, to in effect form a trombone-type seal permitting the axial movement of the actuator tube assembly 41. The adapter 126 also forms a fluid-tight seal between the barrel 121 and the metal tube 127. The metal tube 127 is mounted in a fixed position with respect to the housing 32 and is frictionally retained therein as shown particularly in FIGS. 4 and 8.

A nose cone 131 formed of a suitable material such as Ultem is mounted over the barrel and serves to reinforce the connection between the barrel and the adapter 126 as well as the metal tube 127. The nose cone 131 is threadedly mounted as shown on the distal extremity of the housing 32.

The bore 42 is in axial alignment with the bore 122 provided in the barrel 121 and is adapted to receive tools of various types as hereinafter described. Cooperative means is provided for establishing a fluid-tight seal between the tool and the bore 32 and, as shown in FIGS. 4 and 8, consists of valve means in the form of a valve member of the type described in copending application Ser. No. 07/757,343 filed Sep. 10, 1991. This valve member 136 is seated within a cylindrical enlargement 137 provided at the proximal extremity 46 of the plastic tube 43. A cylindrical cap 138 is threaded onto the cylindrical enlargement 137 (see FIG. 8) to retain the valve member 136 in place. The cap 138 is provided with an annular shoulder 139 which engages the valve member 136 and holds it in place. The annular shoulder 139 is provided with serrations 140 on the proximal surface of the shoulder 139. The cap 138 is provided with a hole 141 which is in registration with the bore 42.

The cap 138 is provided with a bore 142 in alignment with the hole 141. An annular recess 143 is provided within the bore 142.

The housing 32 is also provided with switching capabilities in the form of a switche 151 on the top of the housing 32 which serve electrocautery functions. Switch 151 has three positions, a "central or off" position, and two depressed or "on" positions on opposite sides of the central position. One side of switch 151 is for higher power for cutting and the other side of switch 151 is for lower power for coagulation. Control switches 153 and 154 are provided on opposite sides of the housing in general alignment with the switch 151 and also have three positions the same as switch 151. One side of control switch 153 can be utilized for controlling the introduction of fluids through the bore 42, as for example a saline or other irrigating solution which can be utilized for irrigating and cleansing the area of interest. The other side control switch 153 can be utilized to provide suction in the bore 42 to extract fluids, as for example saline solutions, which have been introduced for irrigation purposes as well as blood, bile, etc. The switch 154 can be utilized for controlling the same functions as switch 153. It can be seen that the switch 151 and the switch 153 have been positioned on the housing so that they can be readily depressed by the index finger on the right hand while the surgical device 31 is being held by the right hand. Similarly the switch 151 and switch 154 can be depressed by the index finger of the left hand when the surgical device 31 is being held by the left hand.

As hereinbefore pointed out the endoscopic device 31 is adapted to be used with tools of the type hereinafter described. In connection with such tools, cooperative mating means is provided whereby the tool is retained within the bore 42 and consists of L-shaped recesses 161 which are formed exteriorly on the cylindrical enlargement 137 of the tube 43. These recesses 161 are adapted to mate with cooperative mating means provided on the tool as hereinafter described. By utilizing cooperative mating means of this type in form of a bayonet-type connection, a tool can be inserted into the bore 42 and locked in place with a small rotational movement. It also can be readily removed by unlocking with a small rotational movement in an opposite direction and subsequent withdrawal.

Figure 10:
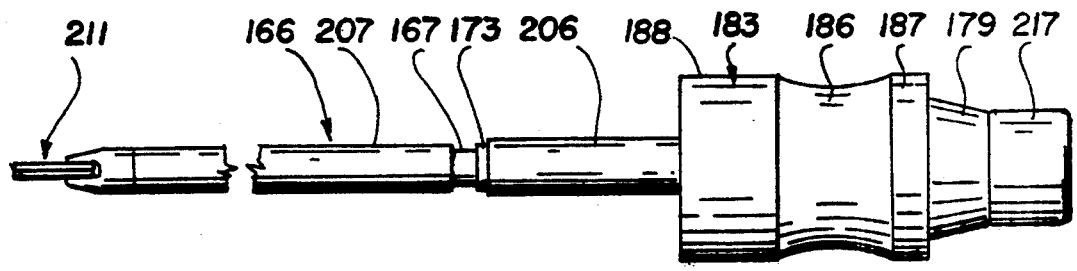
FIG. 10 is a side elevational view of a tool incorporating the present invention.
Figure 11:
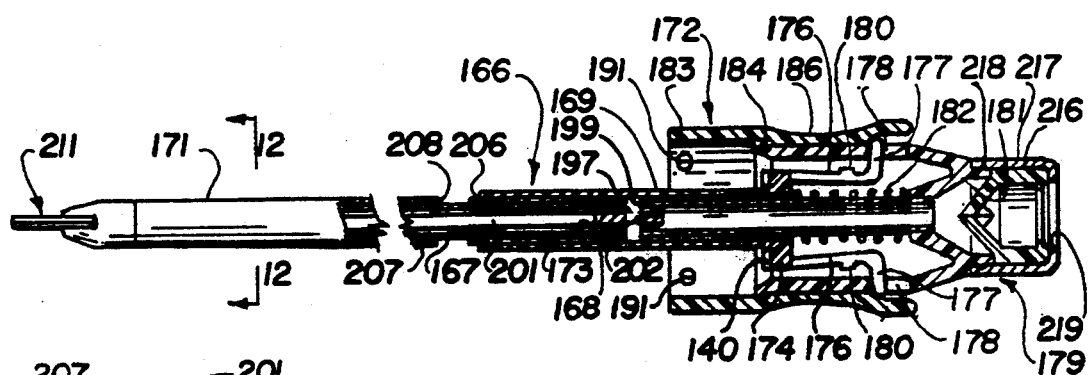
FIG. 11 is a cross-sectional view of the tool shown in FIG. 10.
Figure 12:
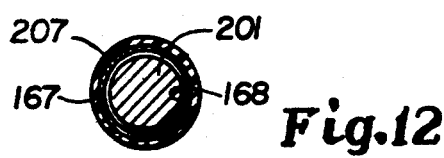
FIG. 12 is a cross-sectional view taken along the line 12—12 of FIG. 11.

As hereinafter described, a plurality of tools are adapted to be utilized with the endoscopic device 31. One of such tools is shown in FIGS. 10, 11 and 12. This tool 166 as shown therein consists of an elongate inner tubular member 167 which is provided with a bore 168 extending axially thereof and therethrough. The inner elongate tubular member can be formed of a suitable material such as stainless steel and can have a suitable exterior diameter such as 3 to 10 mm and by way of example 7 mm, and a suitable interior diameter of 2 to 9 mm and by way of example 6 mm. The tubular member 167 can have a suitable length, as for example ranging from 12 to 20 inches. It is provided with proximal and distal extremities 169 and 171.

A locking and actuation mechanism 172 is mounted on the proximal extremity 169. This mechanism 172 consists of an outer sleeve 173 which is slidably mounted on the proximal extremity 169 of the inner tubular member 167. The proximal extremity of the sleeve 173 is fixed to a slider clip 174. The slider clip 174 is formed of a suitable material such as plastic and is provided with a serrated annulus 175 on its distal extremity adapted to engage the serrations 140 on the cap 138 of the hand held surgical device 31, the slider clip 174 is provided with a pair of arms 176 spaced 180° apart extending parallel to the axis of the sleeve 173. Additional arms 176 can be provided if a further distribution of linear forces is desirable. The arms 176 are substantially L-shaped and are provided with laterally extending legs 177 which extend into slots 178 provided in a cylindrical slider cap 179. The legs 177 are also provided with protrusions 180 which are rectangular in cross-section and extend outwardly so that they are adapted to seat in the annular recess 143 in the cap 138 as hereinafter described. The cylindrical slider cap 179 is provide with an inwardly and distally extending skirt 181 that is secured to the proximal extremity of the inner tubular member 167. Yieldable means in the form of a coil spring 182 is provided on the proximal extremity of the inner tubular member 167 and has one end engaging the skirt 181 and has the other end engaging the slider clip 174 (see FIG. 11).

An outer sleeve 183 formed of a suitable material such as Ultem is coaxially mounted on the slider cap 179 and engages a shoulder 184 provided on the slider cap 179, and is maintained in engagement therewith by a friction fit. The outer surface of the outer sleeve 183 is provided with an annular groove 186 which is arcuate in cross-section, as shown particularly in FIG. 10, that is disposed between the proximal and distal extremities of the outer sleeve 183. As shown in FIG. 11, the proximal extremity 187 is provided with an annular inclined surface 188 that overlies the outwardly extending legs 177 provided on the slider arms 176 to control their outward movement for purposes hereinafter described. The distal extremity 189 is provided with inwardly extending cylindrical protrusions 191 mounted thereon which are adapted to engage the L-shaped recesses 161 provided in the surgical device 31 for forming cooperative locking means between the same in the form of a bayonet-type lock.

A linkage 196 is provided in the tool 166 for actuating mechanisms of the type hereinafter described carried by the tool. This linkage 196 consists of a cylindrical pin 197 which extends diametrically through elongate slots 198 provided in the inner tubular member 167 and into holes 199 provided in the sleeve 173. The slots 198 have their elongations extending in the direction of the axis of the inner tubular member 167. A link rod 201 is mounted within the bore 168 of the inner tubular member 167 and is provided with a hole 202 through which the pin 197 extends. The link rod 201 extends distally from the pin 197 and is used for a purpose hereinafter described. The pin 197 is retained within the holes 199 by a plastic shrink tube 206 formed of a suitable heat-shrinkable plastic and extending over the sleeve 173. Another piece of shrink tube 207 is provided on the portion of the inner tube 167 which is exposed beyond the distal extremity of the sleeve 173 and covers all the distal extremity of the inner tubular member 167 except for a gap 208 which is provided to permit slidable axial movement of the sleeve 173 with respect to the tubular member 167. A mechanism 211 is mounted on the distal extremity of the inner tubular member 167 which is adapted to be operated by movement of the link rod 201 by sliding reciprocal movement of the outer sleeve 173 with respect to the inner tubular member 167.

Sealing means is provided in the proximal extremity of the slider cap 179 and consists of a valve member 216 of the type described in application Ser. No. 07/757,343, filed Sep. 10, 1991, now U.S. Pat. No. 5,141,498 which is clamped in place so that it is in generally axial alignment with the bore 168 of the inner tubular member 167. The valve member 216 is held in place by a cap 217 which threadedly engages a cylindrical extension 218 of the skirt 181 of the slider cap 179. A hole 219 is provided in the cap 217 which is in alignment with the valve member 216 and the bore 168. The valve member serves to form a substantially fluid-tight seal between the cap and the open end of the bore 168 provided in the inner tubular member 167.

Figure 13:
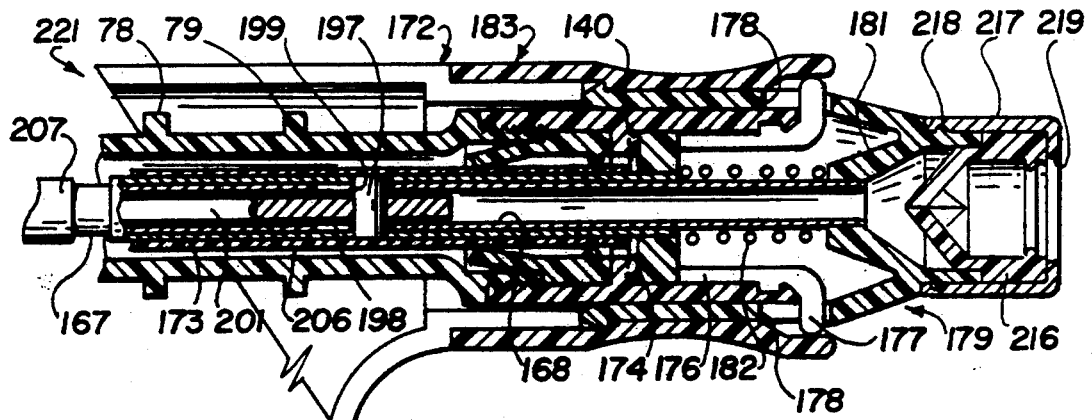
FIG. 13 is a partial cross-sectional view of a device incorporating the present invention with a tool mounted therein.
Figure 23:
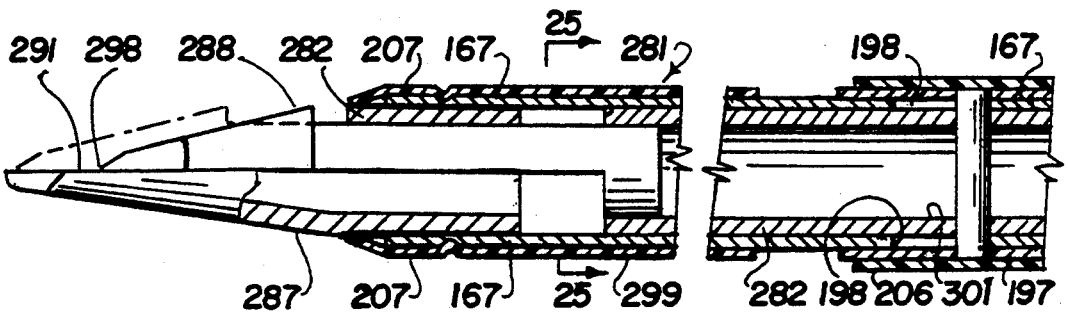
FIG. 23 is a plan view partially in cross-section looking along the line 23—23 of FIG. 22.
Figures 22, 24:
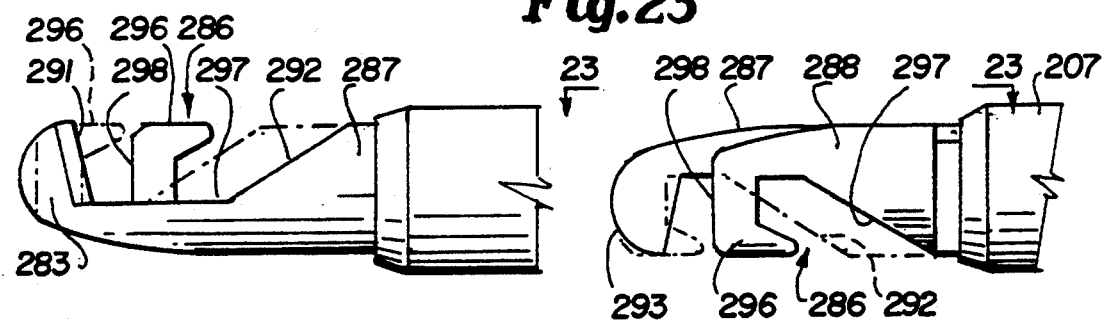
FIG. 22 is a partial side elevational view of another tool incorporating the present invention.
FIG. 24 is a partial side elevational view of the tool shown in FIG. 22 but of the side opposite that shown in FIG. 22.
Figure 25:
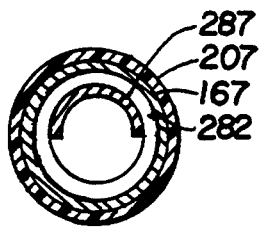
FIG. 25 is a cross-sectional view taken along the line 25—25 of FIG. 23.

The assembly 221 which is formed when a tool 166 is mated with an surgical device 31 is partially shown in FIG. 13. This view shows the manner in which the locking and actuator mechanism 172 of the tool 166 cooperates with the proximal extremity of the surgical device 31. The tool 166 is taken by one hand and the surgical device 31 is grasped by the other hand. The distal extremity of the tool is introduced through the bore 142 and through the valve member 136 and enters into the bore 42 and thence into the bore 122 of the barrel 121. As the locking and actuator mechanism 172 is advanced so that it comes into engagement with the proximal extremity of the housing 32, the tool 166 is rotated until the protrusions 191 come into engagement with the L-shaped recesses 161, then twisted slightly to lock the same into place by bayonet-type connection. At the same time, the proximal extremity of the cap 138 of the actuator tube assembly 41 is moved into the space between the outer sleeve 183 and the legs 177 until the protrusions 180 seat in the annular recess 143 of the cap 138 to lock the cap 138 to the slider clip 174. The serrated annulus 175 engages the serrations 140 on the shoulder 139 so that the tool 166 will be rotated when the actuator tube assembly 41 is rotated. As soon as this has been accomplished, the tool 166 has been locked onto the endoscopy device 31 so that the tool 166 is longitudinally fixed with respect to the endoscopy device 31. When the spool-shaped outer sleeve 183 is locked onto the proximal extremity of the housing 32 of the endoscopy device, the actuator tube assembly 41 can be moved axially with respect to the outer sleeve 183 and can be rotated with respect thereto.

The actuator tube assembly 41 is actuated by movement of the trigger bar 81 through the yoke-like member or lever arm 71 that has the circular extremities 77 disposed between the flanges 78 and 79. Movement of the actuator tube assembly 41, which in turn through its connection between the cap 138 and the protrusions 180 of the arms 176 seated in the annular recess 43 causes movement of the sleeve 173. Movement of the sleeve 173 causes movement of the pin 197 in the slots 198 in the inner tubular member 167 to cause movement of the actuator rod 201. As pointed out previously, only a relatively small amount of axial movement of the actuator tube assembly 41 is required and it is for this reason that the slots 178 and the slots 198 are of a relatively short length. As hereinafter explained, this movement is adequate to operate the mechanism 211 provided on the distal extremity of the tool 166. During the time that the movement of the sleeve 173 takes place, the inner tubular member is held stationary by its engagement with the skirt 181 which is connected by the bayonet-type connection hereinbefore described to the housing 32 of the endoscopy device.

Many of the tools 166 as hereinafter described utilize a common actuation mechanism 231 shown in FIGS. 14–17 that consists of first and second parallel links 232 and 233 which are pivotally connected by a large rivet to the distal extremity of the link rod 201. The other end of the link 233 is connected by a rivet 236 to the leg 237 of an L-shaped scissor blade 238. Similarly, the other end of the link 232 is connected by a rivet 239 to a leg 241 of an L-shaped scissor blade 242. The L-shaped scissor blades 238 and 242 are pivotally mounted on an Allen head screw 243 which is mounted in a tool tip 246 formed of a suitable material such as stainless steel.

The tool tip 246 is formed of parts 246a and 246b. Part 246a is semicircular in form as shown in FIG. 16 and is provided with cylindrical recesses 247 to accommodate the rod 201 to permit reciprocatory movement of the rod 201 therein. The two parts 246a and 246b are mounted in the distal extremity of the tubular member 267 by suitable means such as a crimp fit in the form of annular grooves 248 in the distal extremity of the inner tubular member 167 as shown particularly in FIG. 14. The inner surfaces of the annular grooves 248 frictionally engage the tool tip 246 to retain it in place. The distal extremity of the tool tip 246 is provided with a slot 251 in which the blades 238 and 242 are disposed and which are connected to the links 232 and 233 in the manner hereinbefore described. The part 246b is provided with a well 252 which receives the Allen head screw 243 which is threaded into the part 246a a shown in FIG. 17 to thereby permit pivotal movement of the blades 238 and 242 with respect to the screw 243.

When a tool 166 is free and not disposed within an endoscopy device 31, the yieldable spring 182 will push the rod 201 in a direction towards the distal extremity to the solid-line position shown in FIG. 14 so that the blades 238 and 242 are in the closed position as shown in solid lines. When the tool is placed in the endoscopy device as hereinafter described, the sleeve 173 is moved proximal with respect to the tubular member 167 against the force of the yieldable spring 182 to move the rod 201 towards the proximal extremity to thereby move the rivets 234 to the right as viewed in FIG. 14 to cause the jaws 238 and 242 to be moved to the open dotted-line position shown in FIG. 14. Thereafter, the trigger bar 81 can be moved to actuate the rod 201 to move the scissor blades 238 and 242 to the closed position to perform cutting operations as hereinafter described.

Another tool 256 is shown in FIGS. 18 and 19 which has a proximal extremity which is substantially identical to the tool 166 hereinbefore described. The distal extremity is provided with an actuation mechanism 231 of the type utilized in the tool 166 in which L-shaped jaws 257 and 258 pivotally mounted on the screw 243 replace the L-shaped scissor blades 238 and 242. The jaws 257 and 258 are formed of a suitable material such as stainless steel and are provided with molded coverings 261 and 262 formed of a suitable material such as a hard durable polymeric material. These coverings 261 and 262 are provided with spaced apart serrations or teeth 263 extending transversely of the jaws 257 and 258. As shown in FIG. 19, the molded coverings 261 and 262 are formed to leave an elongate space 264 extending longitudinally of the jaw exposing the stainless steel jaws so that electrocautery functions can be performed as hereinafter explained. Similarly, a space 264 can be provided on the opposite side of the jaw also to serve electrocautery purposes.

Another tool 266 utilizing the actuation mechanism 231 hereinbefore described is shown in FIGS. 20 and 21 and is provided for obtaining biopsy samples. In this tool 266, oval-shaped clam shells 267 and 268 are provided which are pivotally mounted on the screw 243 and which are provided with lever arms 271 and 272 which are connected to the rivets 236 and 239. The clam shells 267 and 268 are formed of a suitable material such as stainless steel. The outer surfaces of the clam shells 267 and 268 can be covered by a layer 276 of an insulating material so that all that remains uncovered is a knife-edge like rim 277 on each of the clam shells to provide a space 278 therebetween through which electrical contact can be made to tissue to perform electrocautery operations as hereinafter described.

In FIGS. 22, 23, 24, and 25 there is shown another tool 281. In this embodiment of the tool, the link member is in the form of a tubular sleeve 282 replacing the rod 201. The tubular sleeve 282 is slidably mounted within the inner tubular member 167 and has its proximal extremity secured to the pin 197 (see FIG. 23) so that as the pin 197 is moved longitudinally in the inner tubular member 167 the sleeve 282 will also be moved. A combination hook and scissor device 286 is mounted on the distal extremity of the inner tubular member 167. This hook and scissor device 286 consists of a fixed part 287 and a movable part 288. The fixed part 287 is provided with a knife edge 291 which is slightly offset upwardly as viewed in FIG. 24 from a line perpendicular to the axis of the inner tubular member 167. The knife edge 291 faces forwardly toward a notch 292 provided in the fixed part 287. The distal or forward extremity of the fixed part 287 is provided with a rounded distal extremity 293. The fixed part 287 is semicircular in cross section as show in FIG. 25 and is fixed to the distal extremity of the inner tubular member 167 by suitable means such as solder (not shown). The movable part 288 is provided with a hook 296 on its distal extremity. The hook 296 is provided with a portion 296a which extends proximally into a cut out 297. The hook 296 is provided with a cutting edge 298 which extends perpendicular to the axis of the inner tubular member 167 which cooperates with the knife edge 291 provided on the fixed part 287. The movable part 288 is secured to the movable sleeve 282 and if desired can be formed integral herewith. A space 299 (see FIG. 23) is provided within the inner tubular member 167 to permit movement of the distal extremity of the sleeve 282 with respect to the proximal extremity of the fixed part 287. Placement of the tool 281 within the endoscopy device 31 causes the sleeve 282 to move to the left as viewed in FIG. 23 so as to move the cutting edge 298 across the knife edge 291 to the dotted-line position shown in FIGS. 22, 23 and 24.

A bore 301 is provided in the sleeve 282 and makes it possible to supply a liquid saline solution into the scissor device 286 in a manner hereinafter described.

Figure 26:
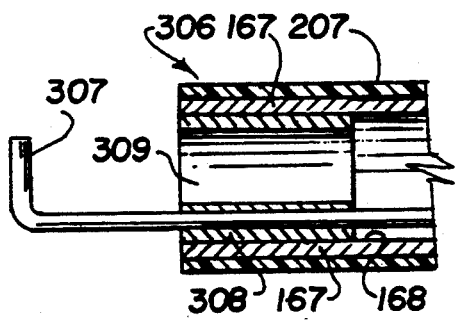
FIG. 26 is a cross-sectional view of the distal extremity of another tool incorporating the present invention.

Another tool 306 is shown in FIG. 26 in which the proximal extremity is similar to that hereinbefore described with respect to the tool 166 with the exception that the pin 197 has been eliminated. In this device, a right angle hook 307 formed of a suitable material such as stainless steel is provided. The hook 307 is mounted in the distal extremity of the inner tubular member 166 in a suitable manner such as by bonding the same into an insert 308 frictionally disposed within the distal extremity of the inner tubular member 167. The insert 308 is provided with a bore 309 that is in communication with the bore 168 in the inner tubular member 167 so that saline solutions can be introduced or suction can be applied to the bore 309 and the bore 168 during use of the tool 306.

Figure 27:
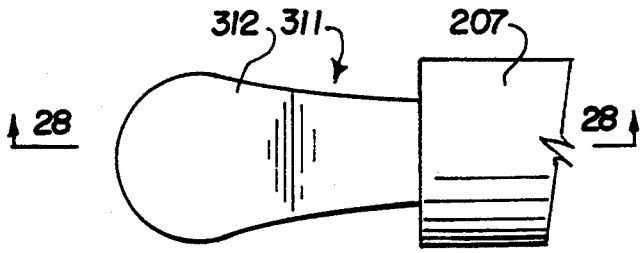
FIG. 27 is a top partial plan view of another tool incorporating the present invention.
Figure 28:
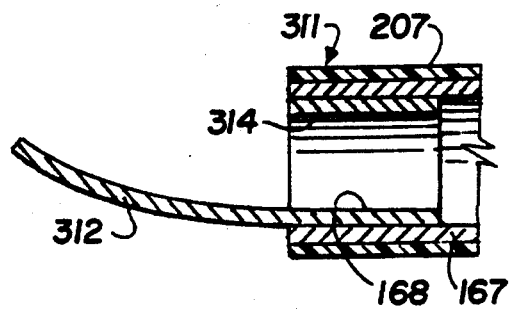
FIG. 28 is a cross-sectional view taken along the line 28—28 of FIG. 27.

Another tool 311 is shown in FIGS. 27 and 28 and serves as a spatula. It is provided with a spatula 312 in the form of a duckbill as shown in FIG. 27. The spatula 312 is formed of a suitable material such as stainless steel. It can be formed as a separate part or formed integral with a stainless steel cylindrical insert 313 which is frictionally retained within the distal extremity of the inner tubular member 167. The spatula 312 alternatively can be formed as a separate piece which can be welded to the cylindrical insert 313. It is inclined upwardly and toward the central axis of the tubular member 167 as shown in FIG. 28. Insert 313 is provided with a bore 314 which is in communication with the bore 168 in the inner tubular member 167 so that the saline solution can be introduced through the bore 314 or alternatively suction can be applied through the bore 314.

Figures 29, 30:
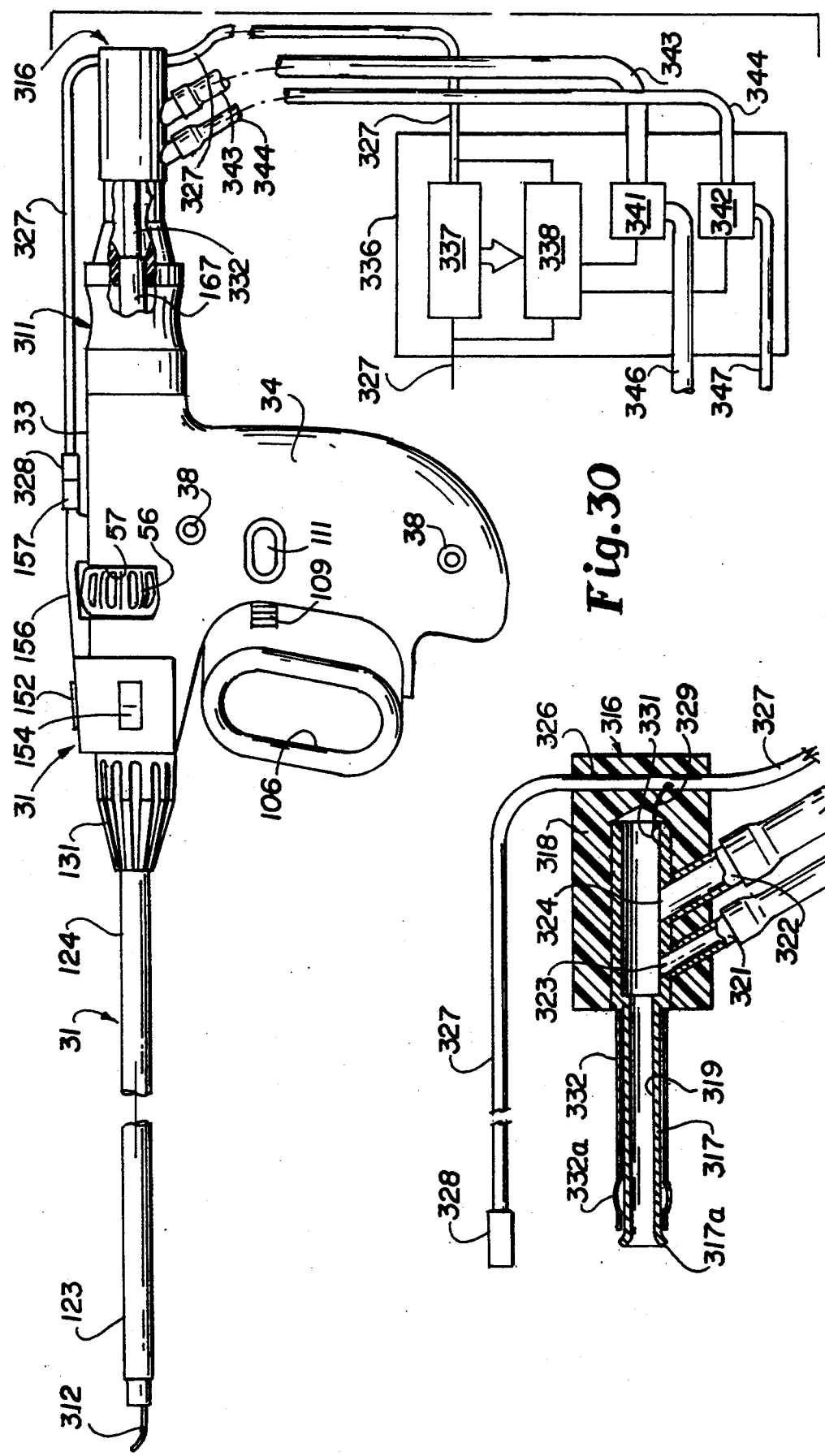
FIG. 29 is a cross-sectional view of an adapter assembly for use with a tool when it is inserted into an endoscopy device of the present invention.
FIG. 30 is a side elevational view of an assembly incorporating the present invention in which a tool is inserted into an endoscopy device and in which an adapter assembly is mounted in the tool.

An adapter assembly 316 which is a type which can be utilized with the tools hereinbefore described and particularly with respect to tool 311 shown in FIGS. 27 and 28 is shown in FIG. 29. This adapter assembly 316 consists of a cylindrical sleeve 317 formed of a suitable material such as stainless steel which is provided with a hub 318. A cylindrical bore extends through the cylindrical sleeves 317 and into the hub 318. Fittings 321 and 322 are mounted on the hub 318 and are provided with flow passages 322, 323 and 324 that are in communication with the bore 319. A covering 226 formed of a suitable insulating material such as plastic is provided over the hub 318 and has molded therein an electrical cable 327 that is provided with multiple conductors as for example seven which extend to a multiple-pin connector 328. The electrical cable 327 also carries another high voltage conductor wire 329 which is utilized in electrocautery procedures as hereinafter described and is electrically connected to the hub 318 by suitable means such as by a solder joint 331. The distal extremity of the cylindrical sleeves 317 is swaged outwardly as shown in FIG. 29 to hold the adapter assembly 36 in place in a tool as hereinafter described. Means is provided for making electrical contact between the inner tubular member 167 and the sleeve 317 and consists of another sleeve 332 formed of a suitable material such as brass which is disposed on the exterior surface of the cylindrical sleeve 317 and extends from the hub 318 to the swaged portion 317a. The sleeve 332 is provided with an annular bulge-like portion 332a to facilitate making electrical contact with the inner tubular member 167 while permitting rotation of the inner tubular member 167 with respect to the sleeve 332.

As shown in FIG. 30, the adapter assembly 16 is adapted to be mounted in the tool 311 and can be advanced through the hole 219 in the cap 17 through the valve member 216 and into the inner tubular member 267 so that the swaged portion 317 makes good electrical contact with the interior of the inner tubular member 167. At the same time, communication is established between the bore 319 and the bore 168 of the tubular member 167. The connector 328 is connected to the connector 157 provided on the endoscopic device 37.

As shown in FIG. 30, a control console 336 is provided for use with the adapter assembly 316. The control console 336 is provided with a microprocessor 337 and relay control assembly 338. The microprocessor 337 and the relay control assembly 338 are connected to a suitable source of power by a cable 339. The microprocessor 327 and the relay panel 338 are connected to the cable 327. The relay panel 338 is also connected to electrical solenoids 341 and 342. The solenoids 341 and 342 are utilized for controlling the flow of fluids to and from the adapter assembly 316. Thus solenoid 341 is provided with a tube 343 which is connected to the fitting 322 provided on the adapter assembly 316 and solenoid 342 is provided with a tube 344 which is connected to the fitting 321 of the adaptor assembly 316. The solenoid 341 is connected to a suitable source of saline solution by a tube 346 and similarly the solenoid 342 is connected to a source of vacuum by tube 347.

Operation and use of the hand held surgical device and tools for use therewith, the assembly thereof and the method may now briefly be described as follows. Let it be assumed that the patient has been prepared and draped for performing a medical procedure, as for example a laparoscopy for removing a diseased gallbladder. The surgeon places a puncture in the abdomen with a small tool such as a Veres needle. Carbon dioxide is introduced into this puncture to cause a partial inflation of the abdomen to thereby create a cavity in the abdominal area. The Veres needle can then be removed, and a trocar can be introduced into the abdomen through the same puncture or in a position adjacent to the needle. The trocar can be of a conventional type or can be of the type described in U.S. Pat. No. 5,176,648. With the trocar in place, additional carbon dioxide is introduced into the abdomen to further inflate the abdomen to a pressure corresponding to approximately 15 mm of mercury. With the abdomen so inflated, an endoscope is inserted into the abdominal cavity so that the interior of the abdominal cavity can be visualized on a video monitor. Thereafter, three additional trocars are positioned in the abdomen, one adjacent the patient's upper left-hand portion of the abdomen, another at the upper right-hand portion of the abdomen, and the third at the lower right-hand portion of the abdomen. These additional sites are used for introduction of various tools typically utilized during endoscopic surgery. For example, the four trocars thus far described would be utilized to remove a gallbladder. The surgeon, after the trocar is in place, takes the endoscopy device 31 of the present invention and grasps it by either his right hand or left hand by grasping the pistol grip-handle portion 34. The surgeon then positions the barrel 121 so that it can enter the trocar and be advanced into the abdomen while the interior of the abdomen is being visualized on the video monitor. The surgeon then selects the desired tool to be utilized with the endoscopy device 31. For example, the first tool the surgeon may select may be a grasper of the type shown in FIGS. 18 and 19. With the grasper 256 locked in place in the endoscopy device 31, the surgeon can manipulate the grasper 256 to manipulate the liver and/or the gallbladder by grabbing onto one of the organs and pulling on it or pushing on it so that the desired positions of the organs are achieved to permit the surgeon to perform the gallbladder removal procedure.

The grasper 256 in its normal position has its jaws 257 and 258 in a closed position. With the jaws in the closed position, the grasper can be inserted through the barrel 121 and the tool locked in place by the cap 138 being advanced between the interior of the slider cap 179 and the legs 76 until the protrusions 180 snap into the annular recess 143 to lock the tool in place. This serves to connect the tool mechanism to the trigger mechanism. Thereafter, upon slight additional inward movement of the grasper 256 the bayonet-type lock connection is made by the protrusions 202 entering into the L-shaped recesses 161 and then with a slight grasper 256 it is locked into place. After this has been accomplished, the trigger bar 81 can be operated by having the fingers of the hand extend through the hole 106 to cause opening and closing of the jaws 257 and 258. When the tool 256 is locked into position as hereinafter described, the jaws 257 and 258 are moved to an open position and thereafter can be opened and closed by the surgeon operating the trigger bar 81.

Movement of the trigger bar from ½ to ⅜" causes approximately ⅛" of travel of the actuator tube assembly 41, which movement is utilized to cause opening and closing of the jaws 257 and 258. Because of the approximately 4-to-1 mechanical advantage which is achieved, the application of one pound of force by the surgeon to the trigger bar 81 will cause the application of approximately 4 pounds of force by the inside surfaces of the grasper jaws 257 and 258. The mechanism for operating the jaws 257 and 258 is one in which pushing of the rod 201 serves to cause closing of the jaws and pulling of the rod 201 causes opening of the jaws 257 and 258. The mechanical advantage is maximized at the point of closure, which is achieved by the pushing toggle action.

After the physician has positioned the liver and gallbladder in the desired positions to achieve access to the desired anatomy, the surgeon can then utilize another tool, as for example another grasper 256, and insert it through one or the other ports to dissect the fatty tissue which is connected to the gallbladder and which is also connected to the cystic duct and to the cystic artery. After the fatty tissue has been pulled away from the desired ducts and arteries, the grasper 256 can be removed from the endoscopy 31 device by giving a slight twist to the tool or grasper 256 to cause the protrusions 191 to move out of engagement with the L-shaped slots 161 and then pulling the tool rearwardly. As the tool is pulled rearwardly, the outer sleeve 183 with its inclined surface 188 urges the arms 176 inwardly so that the protrusions 180 clear the annular recess 143 in the cap 138 to permit separation of the tool from the endoscopy device 31. The tool can be readily removed through the valve member 136 with the valve member 136 retaining a fluid-tight engagement with the tool and, after the tool has been removed, to continue to form a fluid-tight seal with respect to the bore 42 to prevent the escape of carbon dioxide.

Thereafter, the surgeon can take another tool such as a scissors 166 and insert it into the endoscopy device 31 in the same manner in which the grasper tool 256 has been inserted and locked into place. After this has been accomplished, the surgeon can operate the trigger bar 81 of the scissors 166 to cause opening and closing of the scissors to cut a pathway through the cystic duct.

A catheter (not shown) can then be introduced by the surgeon through another trocar and advanced into the ductwork. A radiopaque dye can then be introduced through the catheter into the ductwork, and by viewing the same under x-ray the surgeon can ascertain whether or not in fact he has cut the cystic duct. Assuming that the cystic duct has been severed as desired, another tool can be introduced through a trocar such as a clip applier to apply clips to close the cystic duct. A similar procedure can be utilized for cutting the artery and clipping the same. Once the cystic duct and the artery have been legated, the doctor can cut through the cystic duct and the artery without fear of causing internal bleeding. The gallbladder can then be dissected from the liver by use of the scissor tool 166, the hook 306 or the spatula 12.

In the removal of the gallbladder it may be desirable to use an additional tool or another tool such as the spatula tool 311 shown in FIGS. 27 and 28 with an adapter assembly 316 mounted thereon. After the spatula tool 311 has been introduced into the endoscopy device 31 and locked in place, the spatula 12 can be manipulated to separate the gallbladder from the liver by physical separation utilizing the spatula. Alternatively, electrocautery techniques can be utilized in conjunction with the spatula 312 which by operation of the switches 151 and 152 can be used to burn away the undesired tissue and to perform electrocautery where necessary. The electrical arcing created between the spatula and the tissue will cut through and coagulate away the connective tissue between the gallbladder and the liver. In this way, the gallbladder can be systematically dissected free from the liver.

In the event that there is excessive bleeding or holes are cut into either the gallbladder or the liver, it may be necessary to couterize and cleanse the area in order to permit the surgeon to continue to visualize the operations being performed. This can be readily accomplished by introducing a saline solution by operating one of the switches 153 or 154 provided on the sides of the housing 32 of the endoscopy device. These switches can be operated by the fingers of the hand holding the tool. Thus, first, a saline solution can be introduced into the adapter assembly 316 through the energization of the solenoid 341 to cause fluid to pass into the bore 168 of inner tubular member 167 and through the bore 314. Similarly, suction can be applied to these same passages by energization of the solenoid 342 to cause the saline solution and other liquids in the cavity to be withdrawn from the patient. This can be readily accomplished because of the relatively large-diameter flow passages provided for introducing liquids such as saline solutions and removing liquids from the abdominal cavity.

After the liquids have been removed from the cavity, the surgeon is free to continue the procedure, as for example continuing dissection or removal of the gallbladder from the liver.

After the gallbladder has been separated from the liver, it can be removed from the abdominal cavity through one of the puncture wounds which has been formed in the abdominal wall. Alternatively, the surgeon can utilize a retrieval device such as that disclosed in U.S. Pat. No. 5,190,555, which can be introduced through one of the punctures and the gallbladder and its contents placed into the sack. The sack can then be closed and the sack with its contents, namely the gallbladder, bile and stones, can then be pulled through the abdominal puncture or wound. After the gallbladder has been removed, the other trocars can be removed, as well as the endoscope. The abdomen is then deflated or desufflated. The puncture wounds in the abdomen are then closed with one or more sutures.

In the procedure hereinbefore described, any of the tools hereinbefore described can be utilized in the procedure, as for example the hook scissors tool 286 shown in FIGS. 22–25. Many of the tools can be utilized as electrocautery devices because of the metal distal extremities can form electrical contact with the tissue on which electrocautery operations are to be performed. As explained previously, the adapter assembly 316 can be readily secured to the tool while maintaining a fluid-tight connection with the same through the valve member provided in the tool. Saline introduction and suction operations also can be readily performed. It should be appreciated that surgical device 31 and the tools hereinbefore described can be constructed of non-ferrous materials such as plastic, aluminum, brass, etc., thereby permitting them to be used in conjunction with magnetic resonance imaging, x-rays, CT scanning, ultrasound and other imaging techniques.

From the foregoing it can be seen that there has been provided and endoscopy device which makes it possible to utilize therewith a family of tools in a systems approach necessary for performing many different types of surgical procedures. The hand-held surgical device is constructed in a manner so that various tools can be utilized therewith and actuated in a common manner. Thus, additional application specific tools can be provided for use with the hand held surgical device for use in other body cavities such as the paracardium. Also the hand held surgical device has been constructed in such a manner that it can be sterilized and re-utilized. The tools, also, if desired, can be resterilized and re-utilized. However, they are formed in such a manner so that they can be made relatively inexpensively and disposed of after one use.

What is claimed is:

1. In a hand-held surgical assembly for use in performing a laparoscopic medical procedure, a handle assembly having distal and proximal extremities and having a bore extending therethrough from the distal extremity to the proximal extremity, a tool having tool parts removably mounted in said bore of the handle assembly and having a portion thereof extending out of the proximal extremity of the handle assembly permitting said portion of the tool to be grasped by the human hand to aid in inserting the tool into the bore of the handle assembly from the proximal extremity of the handle assembly and removal of the tool from the handle assembly from the proximal extremity of the handle assembly, cooperative means carried by the handle assembly and the tool for establishing a substantially fluid-tight seal in said bore between said handle assembly and said tool, said tool including an actuation mechanism for operating the tool parts, said handle assembly including hand-operated means adapted to be engaged by the hand and engaging said actuation mechanism of said tool for causing operation of said actuation mechanism of the tool upon operation of the hand-operated means of the handle assembly, means carried by the handle assembly and the tool for retaining the tool in a longitudinal position in the bore while permitting movement of the tool parts of the tool with respect to the handle assembly, cooperative means carried by the handle assembly and the tool for permitting rotational movement of the tool with respect to the hand operated means of the handle assembly and rotation means mounted on the handle assembly and engaging the tool for causing rotational movement of the tool.

2. In a hand-held surgical assembly for use in performing a laparoscopic medical procedure, a handle assembly having distal and proximal extremities and having a bore extending therethrough from the distal extremity to the proximal extremity, a tool rotatably and removably mounted in said bore of said handle assembly and having a portion thereof extending out of the proximal extremity of the handle assembly permitting said portion of the tool to be grasped by the hand to aid in inserting the tool into the bore of the handle assembly from the proximal extremity and removal of the tool from the handle assembly from the proximal extremity, cooperative means carried by the handle assembly and the tool for establishing a substantially fluid-tight seal in said bore between the device and the tool, rotatable means mounted on the handle assembly and engageable by the hand and engaging the tool for rotating the tool, an adapter, means removably and rotatably securing said adapter to said tool whereby said tool can be rotated in the handle assembly while said adapter remains stationary, said tool having a bore therein in communication with the bore in the handle assembly, said adapter having a bore therein in communication with the bore in said tool and means carried by said tool and said adapter for establishing a fluid-tight connection between the bore in said tool and the bore in said adapter.

3. An assembly as in claim 2 together with means for supplying a liquid to said bore in said adapter and a vacuum to said bore in said adapter.

4. A hand-held surgical handle assembly for use with a removable tool in a laparoscopic medical procedure comprising a housing having a proximal extremity, handle means mounted on said housing and adapted to be grasped by the human hand, an actuator tube assembly slidably mounted in said housing for limited slidable movement in said housing and having a bore extending therethrough accessible from the proximal extremity of the housing for receiving the removable tool from the proximal extremity, a barrel carried by said housing and having a bore extending therethrough with the bore being in alignment with the bore in the actuator tube assembly, means carried by the handle means adapted to be engaged by the hand for causing axial movement of the actuator tube assembly with respect to the housing of the handle assembly and valve means mounted in the bore of the actuator tube assembly and adapted to receive said removable tool and to engage said actuator tube assembly for substantially inhibiting the flow of fluid through said bore of the actuator tube assembly.

5. A device as in claim 4 together with coupling means for coupling said barrel to said actuator tube assembly and permitting axial movement of the actuator tube assembly with respect to the barrel.

6. A device as in claim 4 together with means mounted on the housing for rotating the actuator tube assembly.

7. In a hand-held surgical handle assembly for use in a medical procedure, a housing, handle means mounted on said housing and adapted to be grasped by the human hand, an actuator tube assembly slidably mounted in said housing for limited slidable movement in said housing and having a bore extending therethrough, a barrel carried by said housing and having a bore extending therethrough with the bore in the barrel being in alignment with the bore in the actuator tube assembly, means carried by the handle adapted to be engaged by the human hand for causing axial movement of the actuator tube assembly with respect to the housing, valve means mounted in the bore of the actuator tube assembly for substantially inhibiting the flow of fluid through said bore of the actuator tube assembly and coupling means for coupling said barrel to said actuator tube assembly permitting axial movement of actuator tube assembly with respect to the barrel, said coupling means being in the form of a trombone-like connection.

8. A device as in claim 7 wherein said trombone-type connection includes first and second tubes coaxially and slidably mounted on each other.

9. In a surgical tool for use with a hand-held endoscopy handle assembly, an inner elongate tubular member having a bore therein and having proximal and distal extremities, an outer elongate tubular member slidably mounted on the proximal extremity of the inner tubular member, a slider clip secured to the proximal extremity of the outer elongate tubular member, cap means secured to the proximal extremity of the inner tubular member and adapted to be secured to the endoscopy handle assembly for returning the tool locked onto the endoscopy handle assembly, yieldable spring means for yieldably urging the outer elongate tubular member distally of the inner tubular member, means carried by the slider clip adapted to be engaged by the endoscopy handle assembly and for causing relative movement between the outer sleeve and the inner elongate tubular member against the force of the yieldable spring means, a connecting rod mounted in the bore of the inner elongate tubular member, means securing said connecting rod to the outer tubular member whereby as the outer tubular member is slidably moved with respect to the inner tubular member, the connecting rod will be reciprocated, a surgical device mounted on the distal extremity of the inner tubular member and an actuation mechanism connected to the connecting rod and to the surgical device for causing operation of the surgical device.

10. A tool as in claim 9 wherein said slider clip includes at least two arms having protrusions thereon adapted to engage the endoscopy handle assembly, said arms having legs extending outwardly therefrom, said cap means including means for moving said legs to cause said protrusions to move out of engagement with the endoscopy handle assembly when the outer elongate tubular member is moved proximally of the inner elongate tubular member.

11. A tool as in claim 10 wherein said cap means is provided with at least two slots and wherein said legs extend through said slots and wherein said means engaging said legs are in the form of inclined ramps.

12. In a surgical tool for use with a handle assembly, an inner elongate tubular member having a bore therein and having proximal and distal extremities, and an outer elongate tubular member slidably mounted on the proximal extremity of the inner tubular member, connecting rod means disposed within the bore of the inner elongate tubular member and means connecting said connecting rod to said outer elongate tubular member whereby as relative movement occurs between said inner elongate tubular member and said outer elongate tubular member movement of said connecting rod occurs within said inner tubular member, a surgical device mounted on the distal extremity of said inner elongate tubular member and movable between first and second positions, and a toggle linkage connected to said surgical device and said connecting rod whereby as said connecting rod is operated said surgical device is moved between said first and second positions.

13. A tool as in claim 12 wherein said surgical device includes first and second parts pivotally mounted on the distal extremity of said inner elongate tubular member, each of said first and second parts having a lever arm, links pivotally connected to the lever arms of said first and second parts and pivotally connected to said connecting rod whereby as said connecting rod is moved distally of the elongate tubular member, the first and second parts are moved toward closed positions.

14. In a method for performing a medical procedure in a patient by the use of a hand-held endoscopy device having a bore extending therethrough and a plurality of surgical tools, introducing the endoscopy device into the patient, introducing one of the surgical tools through the bore in the endoscopy device and performing a medical operation in the patient, removing the tool, thereafter inserting a different tool through the bore in the endoscopy device and performing an additional medical procedure in the patient, removing the tool after the medical procedure has been completed and thereafter removing the hand-held endoscopy device from the patient.

* * * * *